US005830690A

United States Patent [19]
Gowrishankar et al.

[11] Patent Number: 5,830,690
[45] Date of Patent: Nov. 3, 1998

[54] PROCESS FOR PRODUCING POLYPEPTIDES

[75] Inventors: Jayaraman Gowrishankar; Poonam Bhandari; Kaveti Rajkumari, all of Hyderabad, India

[73] Assignee: Council of Scientific & Indus. Res. & Dept. of Biotech., New Dehli, India

[21] Appl. No.: 578,158

[22] Filed: Dec. 29, 1995

[51] Int. Cl.⁶ .............................. C12N 1/21; C12N 15/64; C12P 19/34; C12P 21/00
[52] U.S. Cl. .................... 435/69.1; 435/91.1; 435/172.3; 435/252.3; 435/252.33; 435/320.1; 536/24.1
[58] Field of Search ............................... 435/91.1, 172.3, 435/252.3, 69.1, 252.33, 320.1; 536/24.1

[56] References Cited

PUBLICATIONS

Igarashi et al., "Bipartite Functional Map of the E. coli RNA Polymerase α Subunit: Involvement of the C–Terminal Region in Transcription by cAMP–CRP", Cell, 65:1015–1022, (1991).
Miller, "Experiments in Molecular Genetics", Cold Spring Harbor Laboratory, (1972), pp. 354,403.
Georgiou et al., "Inclusion Body Formation and the Recovery of Aggregated Recombinant Proteins", in Recombinant DNA Technology and Applications, (ProKop et al., eds.) Inc., Chapter 12, pp. 333–356.
Hockney, "Recent development in heterologous protein production in *Escherichia coli*", TIBTECH, 12:456–463, (1994).
Schein, "Production of Soluble Recombinant Proteins in Bacteria", Bio/Technology, 7:1141–1147, (1989).
Dattananda et al., 1991, J. Bacteriol. 171:1915:1922.
Csonka, 1989, Microbiol. Rev. 53:121–147.
Gowrishankar, 1985, J. Bacteriol. 164:434–445.
May et al., 1986, Mol. Gen. Genet. 205:225–233.
Gowrishankar, 1989, J. Bacteriol. 171:1923–1931.
Gowrishankar, 1990, J. Bacteriol. 172:1165.
Dattananda et al., 1991, J. Bacteriol. 173:7481–7490.
Herbst et al., 1994, Gene 151:137–142.
Gowrishankar et al., 1986, J. Bacteriol. 168:1197–1204.
Faatz et al., 1988, Mol. Microbiol. 2:265–279.
Park et al., 1989, Mol. Microbiol. 3:1011–1023.
May et al., 1989, Mol. Microbiol. 3:1521–1531.
Stirling et al., 1989, Mol. Microbiol. 3:1025–1038.
Sutherland et al., 1986, J. Bacteriol. 168:805–814.
Higgins et al., 1988, Cell 52:569–584.
Jovanovich et al., 1989, J. Biol. Chem. 264:7821–7825.
Ramirez et al., 1989, Proc. Natl. Acad. Sci. USA 86:1153–1157.
Dorman et al., 1989, Mol. Microbiol. 3:531–540.
Prince et al., 1990, J. Biol. Chem. 265:17673–17679.
Ramirez et al., 1991, J. Bacteriol. 173:879–885.
Lucht et al., 1991, J. Bacteriol. 173:801–809.
Ueguchi et al., 1993, EMBO J. 12:1039–1046.
Lucht et al., 1994, J. Biol. Chem. 269:6578–6586.
Tanaka et al., 1994, Biosci. Biotech. Biochem. 58:1097–1101.
Mellies et al., 1994, J. Bacteriol. 176:3638–3645.
Manna et al., 1994, J. Bacteriol. 176:5378–5384.
Sledjeski et al., 1995, Proc. Natl. Acad. Sci. USA 92:2003–2007.
Ding et al., 1995, Mol. Microbiol. 16:649–656.
Csonka et al., 1991, Annu. Rev. Microbiol. 45:569–606.
Lucht et al., 1994, FEMS Microbiol. Rev. 14:3–20.
Overdier et al., 1989, J. Bacteriol. 171:4694–4706.
Overdier et al., 1992, Proc. Natl. Acad. Sci. USA 89:3140–3144.
Owen–Hughes et al., 1992, Cell 71:255–265.
Tupper et al., 1994, EMBO J. 13:258–268.
Fletcher et al., 1995, J. Bacteriol. 177:4508–4513.
Culham et al., 1994, Can. J. Microbiol. 40:397–402.
Sugiura et al., 1992, Mol. Microbiol. 6:1769–1776.
Repoila et al., 1991, Mol. Microbiol. 5:747–755.
Kaasen et al., 1994, Gene 145:9–15.
Lamark et al., 1991, Mol. Microbiol. 5:1049–1064.
Eshoo, 1988, J. Bacteriol. 170:5208–5215.
Jung et al., 1990, J. Biol. Chem. 265:10574–10581.
Gutierrez et al., 1991, J. Mol. Biol. 220:959–973.
Gutierrez et al., 1995, Mol. Microbiol. 16:553–563.
Yim et al., 1994, J. Bacteriol. 176:100–107.
Kempf et al., 1995, J. Biol. Chem. 270:16701–16713.
Csonka, 1982, J. Bacteriol. 151:1433–1443.
Dunlap et al., 1985, J. Bacteriol. 163:296–304.
Nordstrom et al., 1992, Bio/Technology 10:661–666.
Tabor et al., 1985, Proc. Natl. Acad. Sci. USA 82:1074–1078.
Studier et al., 1986, J. Mol. Biol. 189:113–130.
Yansura et al., 1990, Meth. Enzymol. 185: 54–60.
Blackwell et al., 1991, FEBS Letts 295:10–12.
Hanahan, 1983, J. Mol. Biol. 166:557–580.
Vidal–Ingigliardi et al. 1985, Nucleic Acids Res. 13:5919–5926.
Kishore et al., 1994, Ind. J. Biochem. Biophys. 31:249–253.
Raibaud et al., 1984, Gene 29:231–241.
Gutterson et al., 1983, Proc. Natl. Acad. Sci. USA 80:4894–4898.
Winans et al., 1985, J. Bacteriol. 161:1219–1221.
Parker et al., 1988, Gene 73:531–535.
Hamilton et al., 1989, J. Bacteriol. 171:4617–4622.
Deiderich et al., 1992, Plasmid 28:14–24.
Steed et al., 1993, J. Bacteriol. 175:6797–6809.

*Primary Examiner*—Johnny F. Railey, II
*Attorney, Agent, or Firm*—Fish & Richardson P.C.

[57] ABSTRACT

The invention relates to the construction and use of novel expression systems that make use of DNA sequences encoding a promoter or promoters along with cis-regulatory elements, such as those for proU, that permit osmotically inducible initiation of transcription in bacteria; the expression systems of the present invention can be used to efficiently hyperexpress heterologous gene products including proteins or polypeptides; methods for construction of vectors and strains enabling NaCl-induced hyperexpression of heterologous gene products in several organisms such as *Escherichia coli*, and methods for NaCl-induced hyperexpression of heterologous gene products, including proteins or polypeptides, using the said novel combinations in a variety of organisms such as *Escherichia coli*, and further purification of the gene product of interest in either laboratory or industrial scale production systems.

25 Claims, 5 Drawing Sheets

```
         376 (proU)
  SacI     |
GAGCTCGAAT TAATTCCCGC CAAATAGCTT TTTATCACGC AAATAATTTG TGGTGATCTA
CACTGATACT CTGTTGCATT ATTCGCCTGA AACCACAATA TTCAGGCGTT TTTTCGCTAT
CTTTGACAAA AAATATCAAC TTTCTCGATT TGCTCTCAGC CCTTATATCA CGGGAAATTC
CGGCGATTTG CTCGCATCAA TATTCATGCC ACATTTGCCA TCAGGGGTTG CCTCAGATTC
TCAGTATGTT AGGGTAGAAA AAAGTGACTA TTTCCATTGG GTAATATATC GACATAGACA
AATAAGGAA  TCTTTCTATT GCATGGCAAT TAAATTAGAA ATTAAAAATC TTTATAAAAT
ATTTGGCGAG CATCCACAGC GAGCGTTCAA ATATATCGAA CAAGGACTTT CAAAAGAACA
AATTCTGGAA AAAACTGGGC TATCGCTTGG CGTAAAAGAC GCCAGTCTGG CCATTGAAGA
AGGCGAGATA TTTGTCATCA TGGGATTATC CGGCTCGGGT AAATCCACAA TGGTACGCCT
TCTCAATCGC CTGATTGAAC CCACCCGCGG GCAAGTGCTG ATTGATGGTG TGGATATTGC
CAAAATATCC GACGCCGAAC TCCGTGAGGT GCGCAGAAAA AAGATTGCGA TGGTCTTCCA
                       NdeI
GTCCTTTGCC TTAATGCCGC ATATGACCGT GCTGGACAAT ACTGCGTTCG GTATGGAATT
GGCCGGAATT AATGCCGAAG AACGCCGGGA AAAAGCCCTT GATGCACTGC GTCAGGTCGG
GCTGGAAAAT TATGCCCACA GCTACCCGGA TGAACTCTCT GGCGGGATGC GTCAACGTGT
GGGATTAGCC CGCGCGTTAG CGATTAATCC GGATATATTA TTAATGGACG AAGCCTTCTC
GGCGCTCGAT CCATTAATTC GCACCGAGAT GCAGGATGAG CTGGTAAAAT TACAGGCGAA
ACATCAGCGC ACCATTGTCT TTATTTCCCA CGATCTTGAT GAAGCCATGC GTATTGGCGA
CCGAATTGCC ATTATGCAAA ATGGTGAAGT GGTACAGGTC GGCACACCGG ATGAAATTCT
CAATAATCCG GCGAATGATT ATGTCCGTAC CTTCTTCCGT GGCGTTGATA TTAGTCAGGT
ATTCAGTGCG AAAGATATTG CCCGCCGGAC ACCGAATGGC TTAATTCGTA AAACCCCTGG
CTTCGGCCCA CGTTCGGCAC TGAAATTATT GCAGGATGAA GATCGCGAAT ATGGCTACGT
  SacI
TATCGAGCTC
   |
 1631 (proU)
```

PROCESS FOR PRODUCING POLYPEPTIDES

TECHNICAL FIELD

In this patent application, we have described the construction and use of novel expression systems that make use of DNA sequences encoding a promoter or promoters along with cis-regulatory elements, such as those for proU, that permit osmotically inducible initiation of transcription in bacteria. The expression systems of the present invention can be used to efficiently hyperexpress heterologous gene products, including proteins or polypeptides. The invention provides methods for construction of vectors and strains using information available to a skilled artisan in the fields of recombinant DNA technology and bacterial genetics enabling NaCl-induced hyperexpression of heterologous gene products in several organisms such as *Escherichia coli*. The invention also provides methods for NaCl-induced hyperexpression of heterologous gene products, including proteins or polypeptides, using the said novel combinations in a variety of organisms such as *Escherichia coli*, and further purification of the gene product of interest in either laboratory or industrial scale production systems.

PRIOR ART

The proU operon in *Escherichia coli* and its osmotic regulation of transcription.

The proU locus or operon in *Escherichia coli* encodes a binding-protein-dependent transport system for uptake of glycine betaine and L-proline in osmoregulation [Dattananda and Gowrishankar (1989) J. Bacteriol. 171: 1915–1922; Csonka (1989) Microbiol. Rev. 53: 121–147]. Transcription of proU is induced by the addition of NaCl or other impermeable solutes to the growth medium [Gowrishankar (1985) J. Bacteriol. 164: 434–445; May et al. (1986) Mol. Gen. Genet. 205: 225–233; Dattananda and Gowrishankar (1989) J. Bacteriol. 171: 1915–1922]. The nucleotide sequence of proU has been determined in its entirety [Gowrishankar (1989) J. Bacteriol. 171: 1923–1931; Gowrishankar (1990) J. Bacteriol. 172: 1165].

The precise genetic elements required in cis for osmotic regulation of proU expression in *E. coli* have been defined in Dattananda et al. [J. Bacteriol. (1991) 173: 7481–7490]. The plasmid pHYD272 described in this paper identifies the proU 376–~1550 region as being essential for normal osmotic regulation of proU expression. Increased transcription from the region comprising the proU cis regulatory elements during steady-state growth at elevated osmolarity has been shown to be capable of directing the increased production of proteins encoded by certain heterologous genes, such as lacZ or gcdA, that were operatively linked to the said cis regulatory elements [May et al. (1986) Mol. Gen. Genet. 205: 225–233; Dattananda (1993) Ph.D. thesis, Jawaharlal Nehru University, New Delhi, India; Herbs et al. (1994) Gene 151: 137–142]., In addition to the papers cited above, there are others on *E. coli* proU that have described its cloning [Gowrishankar et al. (1986) J. Bacteriol. 168: 1197–1204; Faatz et al. (1988) Mol.Microbiol. 2: 265–279; Park et al. (1989) Mol. Microbiol. 3: 1011–1023], sequencing [May et al.(1989) Mol. Microbiol. 3: 1521–1531; Stirling et al. (1989) Mol. Microbiol. 3: 1025–1038], and mechanism of osmotic regulation [Sutherland et al. (1986) J. Bacteriol. 168: 805–814; Higgins et al. (1988) Cell 52: 569–584; Jovanovich et al. (1989) J. Biol. Chem. 264: 7821–7825; Ramirez et al. (1989) Proc. Natl. Acad. Sci. USA. 86: 1153–1157; Dorman et al. (1989) Mol. Microbiol. 3: 531–540; Ni Bhriain et al. (1989) Mol. Microbiol. 3: 933–942; Prince and Villarejo (1990) J. Biol. Chem. 265: 17673–17679; Ramirez and Villarejo (1991) J. Bacteriol. 173: 879–885; Lucht and Bremer (1991) J. Bacteriol. 173: 801–809; Ueguchi and Mizuno (1993) EMBO J. 13: 1039–1046; Lucht et al. (1994) J. Biol. Chem. 269: 6578–6586; Tanaka et al. (1994) Biosci. Biotech. Biochem. 58: 1097–1101; Mellies et al. (1994) J. Bacteriol. 176: 3638–3645; Manna and Gowrishankar (1994) J. Bacteriol. 176: 5378–5384; Sledjeski and Gottesman (1995) Proc. Natl. Acad. Sci. USA. 92: 2003–2007; Ding et al. (1995) Mol. Microbiol. 16: 649–656]. Some of these findings have also been reviewed [Csonka (1989) Microbiol. Rev 53: 121–147; Csonka and Hanson (1991) Annu. Rev. Microbiol. 45: 569–606; Lucht and Bremer (1994) FEMS Microbioal. Rev. 14: 3–20]. However, all the descriptions in these publications are outside the scope of the invention.

Osmotically regulated systems similar to *E. coli* proU. Several other genes and promoters that are transcriptionally induced by increased osmolarity, similar to those of *E. coli* proU, have been described. *Salmonella typhimurium* has a proU Bacteriol. 168: 805–814; Higgins et al. (1988) Cell 52: 569–584; Overdier et al. (1989) J. Bacteriol. 171: 4694–4706; Stirling et al. (1989) Mol. Microbiol. 3: 1025–1038; Overdier and Csonka (1992) Proc. Natl. Acad. Sci. USA. 89: 3140–3144; Owen-Hughes et al. (1992) Cell 71: 255–265; Tupper et al. (1994) EMBO J. 13: 258–268; Fletcher and Csonka (1995) J. Bacteriol. 177: 4508–4513], and proU-homologous sequences have also been identified in other bacterial genera of the family Enterobacteriaceae [Culham et al. (1994) Can. J. Microbiol. 40: 397–402].

Other genes in *E. coli* and *S. typhimurium* that are transcriptionally induced by osmotic stress and/or by NaCl and whose promoters have been cloned and sequenced include: kdp [Sugiura et al. (1992) Mol. Microbiol. 6: 1769–1776], treA [Repoila and Gutierrez (1991) Mol. Microbiol. 5: 747–755], otsBA [Kaasen et al. (1994) Gene 145: 9–15], bet [Lamark et al. (1991) Mol. Microbiol. 5: 1049–1064; Eshoo (1988) J.Bacteriol. 170: 5208–5215], osmB [Jung et al. (1990) J. Biol. Chem. 265: 10574–10581], osmC [Gutierrez and Devedjian (1991) J. Mol. Biol. 220: 959–973], osme [Gutierrez et al. (1995) Mol. Microbiol. 16: 553–563], and osmY [Yim et al. (1994) J. Bacteriol. 176: 100–107] genes.

In the Gram-positive bacterium *Bacillus subtilis*, the OpuA transporter has been identified which shows marked similarity to the *E. coli* ProU transporter with respect to its structure, function, and osmotic regulation of the cognate genes at the level of transcription [Kempf and Bremer (1995) J. Biol. Chem. 270: 16701–16713]. locus which is homologous to that in *E. coli* in its structure, function and regulation [Csonka (1982) J. Bacteriol. 151: 1433–1443; Dunlap and Csonka (1985) J. Bacteriol. 163: 296–304; Cairney et al. (1985) 164: 1224–1232; Sutherland et al. (1986) J. Bacteriol. 168: 805–814; Higgins et al. (1988) Cell 52: 569–584; Overdier et al. (1989) J. Bacteriol. 171: 4694–4706; Stirling et al. (1989) Mol. Microbiol. 3: 1025–1038; Overdier and Csonka (1992) Proc. Natl. Acad. Sci. USA. 89: 3140–3144; Owen-Hughes et al. (1992) Cell 71: 255–265; Tupper et al. (1994) EMBO J. 13: 258–268; Fletcher and Csonka (1995) J. Bacteriol. 177: 4508–4513], and proU-homologous sequences have also been identified in other bacterial genera of the family Enterobacteriaceae [Culham et al. (1994) Can. J. Microbiol. 40: 397–402].

Other genes in *E. coli* and *S. typhimurium* that are transcriptionally induced by osmotic stress and/or by NaCl and whose promoters have been cloned and sequenced include: kdp [Sugiura et al. (1992) Mol. Microbiol. 6: 1769–1776], treA [Repoila and Gutierrez (1991) Mol. Microbiol. 5: 747–755], otsBA [Kaasen et al. (1994) Gene 145: 9–15], bet [Lamark et al. (1991) Mol. Microbiol. 5: 1049–1064; Eshoo (1988) J.Bacteriol. 170: 5208–5215], osmB [Jung et al. (1990) J. Biol. Chem. 265: 10574–10581], osmC [Gutierrez and Devedjian (1991) J. Mol. Biol. 220: 959–973], osmE [Gutierrez et al. (1995) Mol. Microbiol. 16: 553–563], and osmY [Yim et al. (1994) J. Bacteriol. 176: 100–107] genes.

In the Gram-positive bacterium *Bacillus subtilis*, the OpuA transporter has been identified which shows marked similarity to the *E. coli* ProU transporter with respect to its structure, function, and osmotic regulation of the cognate genes at the level of transcription [Kempf and Bremer (1995) J. Biol. Chem. 270: 16701–16713].

Inducible-promoter-based expression systems.

Inducible promoters have provided the primary means for achieving regulated overproduction by instantaneous induction of syntheis of useful cloned gene products in *E. coli*. In this context, two of the most commonly used systems are: (i) the regulatory system of the *E. coli* lac operon—in this system, the product of the laci repressor gene negatively regulates expression from the lacP promoter or its variants, and induction is achieved by the addition of isopropyl thio-a-D-galactoside (IPTG) or other related inducer at the appropriate time to the culture; and (ii) the regulatory system of bacteriophage lambda—in this system, a mutant lambda cI gene (cI857) that encodes a temperature-sensitive repressor protein negatively regulates expression from the phage lambda PL or PR promoters, and induction is achieved by shifting upward the growth temperature of the culture from 30° C. to 42° C. Regulated expression with either of these inducible promoter-systems has been achieved either directly, by placement of the promoter sequence upstream of the cloned gene, or by one of several different indirect strategies in which the inducible promoter controls the expression of a positive regulatory gene, such as a gene controlling plasmid copy number [Nordstrom and Uhlin (1992) Bio/Technology 10: 661–666], or the phage T7 RNA polymerase gene [Tabor and Richardson (1985) Proc. Natl. Acad. Sci. USA 82: 1074–1078; Studier and Moffatt (1986) J. Mol. Biol. 189: 113–130; Studier et al. (1990) U.S. Pat. No. #4,952,495], in a two-tier system of regulation.

Alternative inducible promoters for achieving these objectives have also been described, for example the trp promoter [Yansura and Henner (1990) Meth. Enzymol. 185: 54–60] or the pH-inducible promoter [Tolentino et al. (1992) Biotech Lett. 14: 157–162], but these have neither been as well developed or as widely used as the two methods described above.

DEPOSIT

In compliance with the requirements of full disclosure, two plasmids of this invention have been deposited in the National Collections for Industrial and Marine Bacteria Limited, Scotland, United Kingdom (NCIMB), prior to the filing date of this application The two plasmids are pHYD272 and pHYD501. The deposit made is of the strain DH5/pHYD272/pHYD501, under the culture deposit number NCIMB 40772 dated 2nd Oct. 1995.

SUMMARY OF THE INVENTION

The present invention relates to the use of DNA sequences encoding a promoter or promoters along with cis regulatory elements that permit NaCl-inducible or osmotically inducible initiation of transcription from the said promoter or promoters in a bacterium, for constructing expression vector systems for the production by instantaneous induction of the products of heterologous genes in the said bacterium; a process for expressing heterologous gene encoding a useful heterologous gene product; a recombinant DNA comprised of a first DNA segment linked in cis to a second DNA segment, and a transformed bacterium harbouring the recombinant DNA construct which either (i) integrated into the bacterial chromosome or (ii) present on a recombinant plasmid or phage vector that is capable of autonomous replication within the said bacterium.

DESCRIPTION OF THE INVENTION

Accordingly, the present invention provides an use of DNA sequences encoding a promoter or promoters along with cis regulatory elements that permit NaCl-inducible or osmotically inducible initiation of transcription from the said promoter or promoters in a bacterium, for constructing expression vector systems for the production by instantaneous induction of the products of heterologous genes in the said bacterium.

The invention also relates to an expression vector system for the production by instantaneous induction of the products of heterologous genes in a bacterial species within the family Enterobacteriaceae and which either is comprised of a plasmid or bacteriophage construct that can replicate in the said bacterial species, or can be integrated by known methods into the chromosome of the said bacterial species. Preferably, the bacterial species is *Escherichia coli*.

The invention further provides a process for expressing a heterologous gene encoding a useful heterologous gene product such as RNA or polypeptide, comprising the steps of:

(a) obtaining a first DNA segment that carries the sequence encoding the said useful heterologous gene product and obtainable by known methods;

(b) obtaining a second DNA segment that carries the sequence encoding a promoter or promoters along with cis regulatory elements that permit NaCl-inducible or osmotically inducible initiation of transcription from the said promoter or promoters in a bacterium, and obtainable by known methods;

(c) constructing, by known recombinant DNA methods, a vector capable of delivering a recombinant DNA construct for stable maintenance within the said bacterium, the said recombinant DNA construct being comprised of the said first and second DNA segments linked togther in cis in such a manner that transcription of the said heterologous gene in transformed cells of the said bacterium is exclusively or nearly exclusively directed by the said promoter or promoters;

(d) using the said vector to obtain, by known methods, transformed cells of the said bacterium which have stably inherited the said recombinant DNA construct;

(e) growing the recombinant transformed bacteria in low-osmolarity medium using known methods;

(f) inducing the synthesis of the said useful heterologous gene product by addition to the culture of an osmolyte such as NaCl; and (g) isolation, purification and characterisation of the said useful gene product by known methods.

The preferred aspect of the invention is that the second DNA segment carries the *Escherichia coli* proU DNA sequence or a part thereof, or any DNA sequence that has similarity of at least 80% with the *Escherichia coli* proU DNA sequence or a part thereof, and the bacterium belongs to a bacterial species within the family Enterobacteriaceae, for example *Escherichia coli*.

Further, the invention relates to a recombinant DNA construct comprised of (i) a first DNA segment that carries the sequence encoding a promoter or promoters along with cis regulatory elements that permit NaCl-inducible or osmotically inducible initiation of transcription from the said promoter or promoters in a suitable host bacterium, linked in cis to (ii) a second DNA segment that carries the sequence encoding a transcription-activator protein, such that synthesis of the said protein will be activated, in derivatives of the said bacterium carrying the said recombinant construct, by the addition of NaCl or other osmolyte to the medium.

The preferred aspect of the invention is that the recombinant DNA construct having the first DNA segment carries the *Escherichia coli* proU DNA sequence or a part thereof, or any DNA sequence that has similarity of at least 80% with the *Escherichia coli* proU DNA sequence or a part thereof and the transcription-activator protein is an enzymatically active RNA polymerase of bacteriophage T7.

The invention also provides a BamHI-ended DNA fragment representing a recombinant DNA construct comprised of (i) the cis regulatory elements of proU derived from *Escherichia coli* and obtainable from plasmid pHYD513 on a PstI-EcoRI fragment, linked in cis to (ii) a DNA segment encoding enzymatically active T7 RNA polymerase and which segment is present on the larger of the two fragments obtainable from plasmid pHYD501 following PstI-EcoRI digestion; and the said BamHI-ended DNA fragment is obtainable from plasmid pHYD503.

Preferably, the said recombinant DNA construct being either (i) integrated into the bacterial chromosome or (ii) present on a recombinant plasmid or phage vector that is capable of autonomous replication within the said bacterium. The bacterium may be selected from *Escherichia coli*, preferably the *Escherichia coli* strain GJ1150, in which the BamHI-ended DNA fragment is integrated into the ma1PQ locus of the chromosome.

Furthermore, the invention provides a process for obtaining a transformed bacterium harbouring a recombinant DNA construct, comprising the steps of:

I. preparing the recombinant DNA construct, comprising the steps of: (a) obtaining and cloning by known methods a first DNA segment that carries the sequence encoding a promoter or promoters along with cis regulatory elements that permit NaCl-inducible or osmotically inducible initiation of transcription from the said promoter or promoters in a suitable host bacterium; (b) linking by known methods the said first DNA segment with a second DNA segment that carries a sequence encoding a transcription-activator protein such that synthesis of the said protein, in derivatives of the said host bacterium carrying the said recombinant DNA construct, is exclusively or nearly exclusively dependent on transcription initiated from the said promoter or promoters; and also such that the said recombinant DNA construct is covalently contiguous with the DNA sequence of a vector such as plasmid or phage; (c) transforming the ligation mixture into a suitable strain in which the said vector can replicate autonomously and be maintained; and (d) identifying clones carrying the correct recombinant construct by known methods; and II. obtaining by known methods a transformed derivative of the said host bacterium in which the said recombinant DNA construct is either (i) integrated into the bacterial chromosome or (ii) present on a recombinant plasmid or phage vector that is capable of autonomous replication within the said host bacterium.

The first DNA segment of the process carries the *Escherichia coli* proU DNA sequence or a part thereof, or any DNA sequence that has similarity of at least 80% with the *Escherichia coli* proU DNA sequence or a part thereof, and the transcription-activator protein is an enzymatically active RNA polymerase of bacteriophage T7.

Preferably, the present process as applied to a recombinant DNA construct comprised of an *Escherichia coli* proU-T7 RNA polymerase fusion, wherein the bacterium is *Escherichia coli*; the first DNA segment carries the *Escherichia coli*-derived proU cis regulatory elements and is obtainable from plasmid pHYD513 or pHYD514 by PstI-EcoRI digestion; the second DNA segment carries a sequence encoding an enzymatically active T7 RNA polymerase and is present on plasmid pHYD501; the recombinant DNA construct is generated by ligating the PstI-EcoRI-ended first DNA segment with the larger of the two fragments generated following PstI-EcoRI digestion of plasmid pHYD501; and plasmids carrying the said recombinant DNA construct, such as pHYD503, are identified by known methods following transformation of a suitable strain with the ligation mixture and selection for tetracycline-resistance.

The present invention, in addition, relates to a process for obtaining integration of the recombinant DNA construct comprised of an *Escherichia coli* proU-T7 RNA polymerase fusion, into the ma1PQ locus of the *Escherichia coli* chromosome, comprising the steps of:

(a) ligating the BamHI-ended DNA fragment carrying the proU-T7 RNA polymerase fusion and obtainable from plasmid pHYD503, with BglII-digested pOM41 DNA;

(b) identifying recombinant plasmids, such as pHYD507, in which the proU promoters on the insert are transcribed in the same direction as the promoter-less tet gene in pOM41;

(c) transforming the said recombinant plasmid into strain pop2249 and identifying derivatives that are tetracycline-resistant, ampicillin-resistant and Lac- at low osmolarity, in which the proU-T7 RNA polymerase fusion construct has been transferred by reciprocal homologous recombination into the ma1PQ locus;

(d) subsequently identifying integrant colonies, such as GJ1150, in which the ampicillin-resistance and tetracycline-resistance markers have been lost following spontaneous loss of the pOM41-derived plasmid replicon; and (e) optionally transferring, by known methods of gene transfer and homologous recombination, the ma1PQ locus carrying the integrated proU-T7 RNA polymerase fusion construct from these integrant strains into other strains of *Escherichia coli*.

Moreover, the present invention also provides a process for expressing a heterologous gene encoding a useful heterologous gene product such as RNA or polypeptide, comprising the steps of:

(a) obtaining a first DNA segment that carries a sequence encoding the said useful heterologous gene product and obtainable by known methods;

(b) constructing, by known recombinant DNA methods, a vector capable of being delivered into and maintained within a suitable host bacterium, in which the said DNA fragment is cloned in the correct orientation downstream of a first promoter that is activatable by a transcription-activator protein such that synthesis of the said useful gene product within transformed cells of the said bacterium is exclusively or nearly exclusively dependent on transcription initiated from the said first promoter; (c) obtaining, by known methods, transformed cells of the said bacterium which carry both: the said vector, and additionally a recombinant DNA construct comprised of: (i) a second DNA segment that carries the sequence encoding a second promoter or promoters along with cis regulatory elements that permit NaCl-inducible or osmotically inducible initiation of transcription from the said second promoter or promoters in the said bacterium, linked in cis to (ii) a third DNA segment that carries a sequence encoding the said transcription-activator protein, such that synthesis of the said protein will be activated, in derivatives of the said bacterium carrying the said recombinant construct, by the addition of NaCl or other osmolyte to the medium;

(d) growing the recombinant transformed bacteria in low-osmolarity medium using known methods;

(e) inducing the synthesis of the said useful gene product by addition to the culture of an osmolyte such as NaCl; and (f) isolation, purification and characterisation of the said useful gene product by known methods.

Although regulated expression systems that make use of lac- or phage lambda-derived promoters for overproduction of cloned gene products are effective and convenient and have been extensively exploited for the overproduction of products of cloned genes in laboratory-scale *E. coli* cultures, there are certain problems associated with each of them particularly in relation to their use with very large volumes of bacterial cultures. With the lac regulatory system, the problem has to do with the high cost of the chemical IPTG which is required for achieving induction, and with the fact that several commercially available batches of IPTG also have a significantly high concentration of the toxic and environmentally unfriendly chemical, dioxane [Sigma Chemical Company Catalog (1995): 596]. With the phage lambda regulatory system, the main problem is one of being able to achieve temperature-upshift of large volumes of culture relatively rapidly without causing significant killing of cells by direct contact with the heat source; furthermore, the overproduction of several proteins in *E. coli* leads to the formation of insoluble inclusion bodies, a problem which appears to be accentuated upon incubation of cultures at the higher temperature. Thus, there is an as yet unfulfilled need for the development of efficient alternative processes, including vectors and appropriate host strains, to achieve the regulated overexpression of the products of cloned genes in bacteria such as *E. coli*.

The potential advantages of regulated expression systems that employ NaCl or other osmolyte as inducers, over those that employ either IPTG or temperature-upshift for induction, have not so far been recognized in the art. This conclusion is evident also from the fact that the only widely employed inducible overexpression systems that employ *E. coli* as the host organism are ones that make use of the IPTG- or the temperature-inducible lac-derived or phage lambda promoters respectively. These advantages include, but are not restricted to, the following: (i) The cost of inducer is extremely low. (ii) Even relatively impure preparations of inducer may be used. (iii) Nearly instantaneous induction can be achieved at low cost in all cells even in large cultures. (iv) Production of inducer is not associated with synthesis of potential environmental pollutants. (v) The addition of NaCl or other osmolyte as inducer to cultures growing in complex medium will permit the cytoplasmic accumulation of glycine betaine, under which conditions the problems of inclusion-body formation with certain hyperexpressed proteins would be mitigated [Blackwell and Horgan (1991) FEBS Lett. 295: 10–12].

The present invention describes processes by which the novel use of NaCl or other osmolytes as inducer for regulated overproduction by instantaneous induction of heterologous gene products in bacteria is reduced to practice. The processes of the present invention make use of a promoter (with associated cis regulatory elements) that is NaCl-inducible or osmotically inducible in transformed cells of a suitable host bacterium, to direct the expression of a target gene encoding a useful gene product. This may be achieved by a direct strategy, wherein the said promoter with associated cis regulatory elements are operatively linked in cis to the said target gene within transformed cells of the said suitable host bacterium.

The process of the present invention wherein the said direct strategy is used comprises the steps of:

(i) the identification and cloning of a promoter (with associated cis regulatory elements) that is NaCl-inducible or osmotically-inducible in a suitable host bacterium;

(ii) the identification and cloning of a target gene;

(iii) creating an operon fusion by operatively linking the said NaCl-inducible or osmotically-inducible promoter in cis to the target gene along with other appropriate signals such as those for translation-initiation, in such manner that synthesis of the said target gene product in transformed cells of the said bacterium is exclusively or nearly exclusively dependent on transcription initiated from the said NaCl-inducible or osmotically-inducible promoter;

(iv) obtaining transformed cells of the said bacterium by delivering, and maintaining, the said operon fusion within the cells of the said bacterium;

(v) growing the said transformed cells in a low-osmolarity culture medium and inducing the synthesis of the said target gene product by the addition of NaCl or other osmolyte to the said medium;

(vi) demonstrating that the said target gene product is substantially induced under these conditions; and (vii) making an enriched or purified preparation of the said target gene product from the said culture medium.

In the examples below, we have provided the details of the process confining to one particular set of embodiments of this invention that employs the direct strategy outlined above, in which the said NaCl-inducible or osmotically-inducible promoter is derived from the *Escherichia coli* proU locus; the chosen example of the said useful target gene product is the RNA polymerase of bacteriophage T7; and the said host bacterium is *Escherichia coli*. The description in the text inclusive of these examples, taken in combination with the materials and methods available in the prior art to a skilled artisan in the field, constitute a full disclosure of the invention with respect to the direct strategy indicated above.

We have also developed an indirect strategy to obtain the regulated overproduction, with the use of NaCl or other osmolyte as inducer, of heterologous target gene products in a suitable host bacterium. In this indirect strategy, a promoter (with associated cis regulatory elements) that is NaCl-inducible or osmotically inducible in transformed cells of the said bacterium is operatively linked in cis to a gene encoding a transcription-activator protein. The resulting novel recombinant construct is present in transformed cells of the said bacterium, which cells are also manipulated to carry a second recombinant construct comprised of a promoter, from which transcription is activated by the said transcription-activator protein, operatively linked in cis to a target gene.

The process of the present invention wherein the said indirect strategy is used comprises the steps of:

(i) the identification and cloning of a promoter that is NaCl-inducible or osmotically-inducible in a suitable host bacterium;

(ii) the identification and cloning of a gene for a transcription-activator protein that is capable of functioning as transcription activator in the said bacterium;

(iii) the identification and cloning of a second promoter, transcription from which will be specifically activated by the said transcription-activator protein in the said bacterium;

(iv) the identification and cloning of a target gene;

(v) linking the said NaCl-inducible or osmotically-inducible promoter to the gene for the said transcription-activator protein in a novel recombinant construct, along with other appropriate signals such as those for translation-initiation, and in such a manner that synthesis of the said transcription-activator protein, in transformed cells of the said bacterium, is almost exclusively dependent on transcription initiated from the said NaCl-inducible or osmotically-inducible promoter;

(vi) linking the said second promoter to the said target gene in a second recombinant construct, along with other appropriate signals such as those for translation-initiation, and in such manner that synthesis of the said target gene product, in transformed cells of the said bacterium, is directed from transcripts initiated at the said second promoter;

(vii) obtaining transformed cells of the said bacterium by delivering, and maintaining, the said novel recombinant construct and the said second recombinant construct within the cells of the said bacterium;

(viii) growing the said transformed cells in a low-osmolarity culture medium and inducing the synthesis of the said target gene product by the addition of NaCl or other osmolyte to the said medium;

(ix) demonstrating that the said target gene product is substantially induced under these conditions; and (x) making an enriched or purified preparation of the said target gene product from the said culture medium.

In the examples below, we have provided the details of the process confining to one particular set of embodiments of this invention that employs the indirect strategy outlined above, in which the said NaCl-inducible or osmotically-inducible promoter is derived from the *Escherichia coli* proU locus; the said transcription-activator protein is phage T7 RNA polymerase; the said second promoter is the m10 promoter of phage T7; the said target gene is *E. coli* ssb, that encodes the SSB protein; and the said host bacterium is *Escherichia coli*. The descriptions in the text inclusive of the examples, taken in combination with the materials and methods available in the prior art to a skilled artisan in the field, constitute a full disclosure of the invention with respect to the indirect strategy indicated above.

The regulated expression systems that have been disclosed in this invention, which employ NaCl or other osmolyte for instantaneous induction, offer certain generic advantages over expression systems in which the inducer is continuously present in the culture during steady-state growth. This is because transformed host cells that are designed to overproduce a cloned gene product during steady-stage growth often grow extremely poorly under the said steady-state growth conditions and are rapidly overtaken in culture by mutants in which the level of expression of the cloned gene has been reduced. With regulated expression systems that employ instantaneous induction (such as those disclosed in this invention), the phase of growth of the bacterial culture and that of increased expression of the cloned gene product are separated in time and can then be individually optimized.

The examples listed below describe: (i) the construction of plasmids pHYD513 and pHYD514 (example 1), in which the cis regulatory elements of *E. coli* proU are resident on a "cassette DNA sequence" flanked by convenient restriction enzyme cut-sites such that the cassette can easily be linked either (a) directly to a target gene, in pursuit of the direct strategy indicated above, or (b) to a gene encoding a transcription-activator protein., in pursuit of the indirect strategy indicated above; (ii) the construction of plasmid pHYD503, in which the cassette from pHYD513 carrying the cis regulatory elements of *E. coli* proU is operatively linked in cis to the gene encoding phage T7 RNA polymerase to generate a novel recombinant construct, as also a practical demonstration of the direct strategy indicated above, by describing the overproduction following NaCl addition of phage T7 RNA polymerase in *E. coli* cells transformed with pHYD503 (example 2); (iii) the transfer of the said novel recombinant construct from pHYD503 into the ma1PQ locus on the chromosome of *E. coli* so as to obtain a stable single-copy integrant strain GJ1150 (example 3); and (iv) the use of strain GJ1150 to direct the NaCl-induced overproduction, by the indirect strategy indicated above, of the SSB protein, from a plasmid in which the *E. coli* ssb gene (target gene) is fused to the T7 m10 promoter (example 4).

In the following examples, the following materials and methods were used throughout:

1. The strains DH5[as described by Hanahan (1983) J. Mol. Biol. 166: 557–580 and Bethesda Research Labs, (1986) Focus 8: 9]; BL21 [as described by Studier and Moffatt (1986) J. Mol. Biol. 189: 113–130]; and pop2249 [as described by Jung et al. (1990) J. Biol. Chem. 265:10574–10581], were used as bacterial strains and hosts for plasmids.

2. The plasmids used were pBluescript-KS (Stratagene GmbH, Postfach 10 54 66, D-6900, Heidelberg, FRG);

pGEM-3Z (Promega Corporation, 2800, Woods Hollow Road, Madison, WI 53711–5399, USA); pOM41 [Vidal-Ingigliardi and Raibaud (1985) Nucleic Acids Res. 13: 5919–5926]; pGK2 [Kishore et al. (1994) Ind. J. Biochem. Biophys. 31: 249–253]; pHYD272 [Dattananda et al. (1991) J. Bacteriol. 173: 7481–7490]; and pHYD501.

3. The growth medium used was LBON medium (Bactotryptone 10.0 g/l, Bacto yeast extract 5.0 g/l, pH adjusted to 7.0). Antibiotics were used (when needed) at the following final concentrations (fg/ml) : ampicillin (Amp), 100; tetracycline (Tet), 15; and trimethoprim (Tp), 60. Superscripts r and s are used to denote the phenotypes of resistance and sensitivity respectively. 5-bromo-4-chloro-3-indolyl-a-D-galactoside (X-gal) was used in plates at a final concentration of 25 fg/ml. Stock solutions of ampicillin and tetracycline were prepared in water and ethanol respectively; and those of trimethoprim and X-gal in dimethylformamide.

4. The media, chemicals and antibiotics were obtained from Sigma (P.O. Box 14508, St. Louis, Mo. 63178, USA); Difco Laboratories (P.O. Box 331058, Detroit, Mich. 48232-7058, USA); and Hi Media Laboratories Pvt. Ltd. (23, Vadhani Industrial Estate, Bombay 400086, India).

5. Restriction endonucleases and enzymes used during DNA cloning were obtained from New England Biolabs Inc. (32 Tozer Road, Beverly, Mass. 01915-5599, USA); Boehringer Mannheim GmbH (Biochemica P.O. Box 310 120, D-6800 Mannheim 31, FRG); Promega Corporation (2800, Woods Hollow Road, Madison, Wis. 53711–5399, USA); and Bangalore Genei Pvt. Ltd. [No. 277, 2nd Main (Sankey Road) , 18th Cross, Malleswaram, Bangalore-560003, India]. The Geneclean kit, for purification of DNA fragments separated by electrophoresis on agarose gels, was purchased from Bio101 Inc. (P.O. Box 2284, La Jolla, Calif. 92038-2284, USA).

6. Unless mentioned otherwise, the preparation and cloning of DNA fragments was by standard techniques as described in Molecular Cloning: A laboratory manual, Second Edition (1989) by Sambrook et al. Cold Spring Harbor Laboratory Press, Cold. Spring Harbor, N.Y.

7. The protein profiles of total cell lysates were obtained using the the standard techniques as described in Molecular Cloning: A laboratory manual, Second Edition (1989) by Sambrook et al. Cold Spring Harbor Laboratory Press, Cold Spring Harbor, N.Y.

EXAMPLE 1

Figure 1:
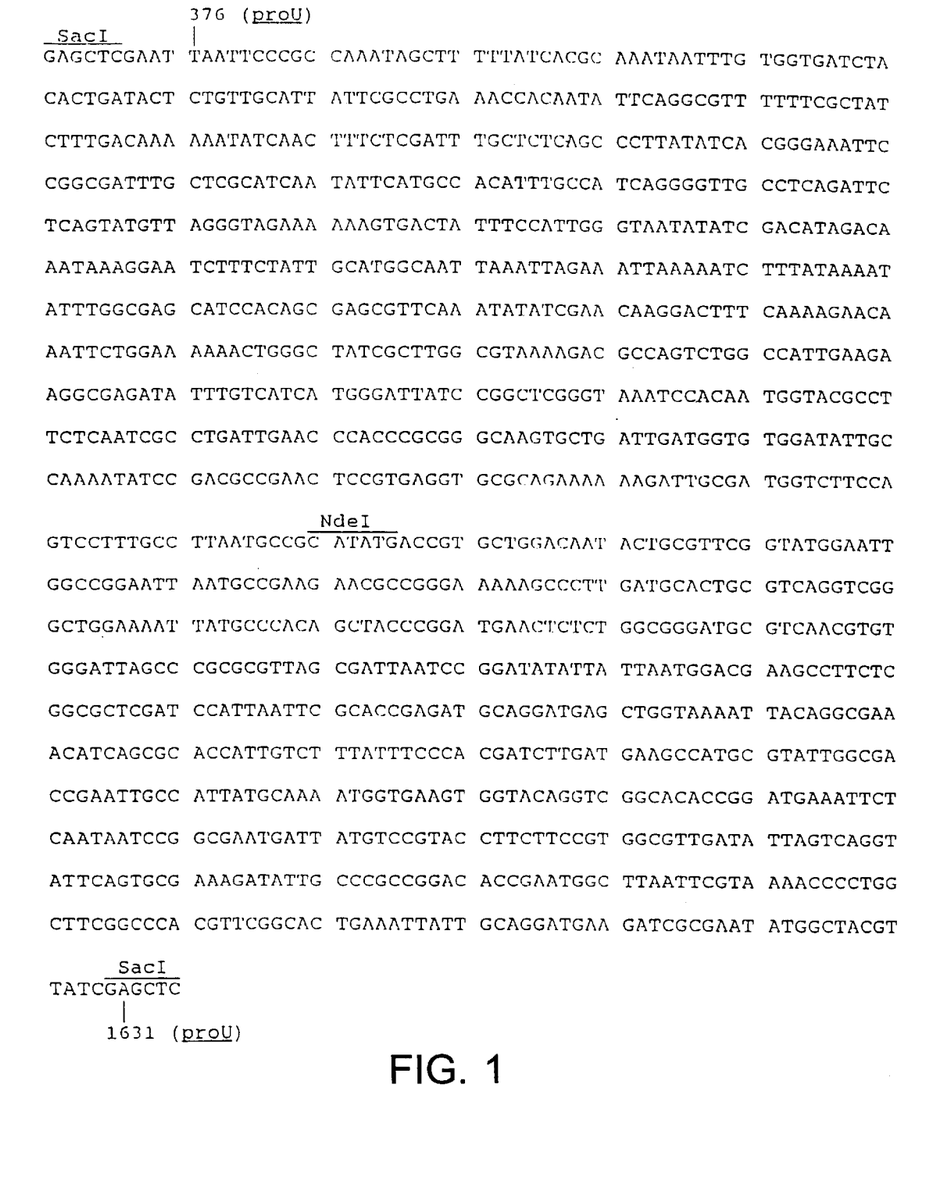
FIG. 1 depicts the nucleotide sequence of the SacI fragment (SEQ ID NO:1) from plasmid pHYD272 comprising the *E. coli* proU sequence from positions 376 to 1631.

Construction of plasmids pHYD513 and pHYD514 harbouring cis regulatory regions of proU flanked by convenient restriction enzyme sites The plasmid pHYD272 is an IncW-replicon-based low-copy-number plasmid encoding Tp<sup>r</sup> as the selective marker and which carries the the proU sequence from nucleotide 376 to ~1550, harbouring the two proU promoters and other regulatory sequences which are sufficient and necessary for conferring normal osmotic inducibility of transcription initiated from the two promoters [Dattananda et al. (1991) J. Bacteriol. 173: 7481–7490]. The nomenclature for nucleotide number designations in the proU locus is taken from that described [Gowrishankar (1989) J. Bacteriol. 171: 1923–1931, read along with Erratum (1990) 172: 1165]. We have subsequently identified the right end of the proU sequence in pHYD272 to lie at position 1631 (see FIG. 1—depicting the nucleotide sequence of SacI fragment from plasmid pHYD272 comprising the E. coli proU sequence from positions 376 to 1631; the two ends of the proU sequence are marked by the corresponding nucleotide number designations; overlined are the SacI ends of the fragment and the NdeI site at position 1045–1050) . For easy manipulation of proU regulatory sequences, this 1.25-kb fragment from pHYD272 was cloned into the multiple-cloning-site of the high-copy-number plasmids pBluescript-KS and pGEM-3Z. For this purpose, the plasmid pHYD272 was digested with the restriction enzyme SacI to release the 1.25-kb proU fragment (see FIG. 1), and this was then subcloned into the SacI site of each of the vectors pBluescript-KS and pGEM-3Z. The resulting plasmids were designated as pHYD511 and pHYD514 respectively.

In another variation of these constructs, the NdeI site present at position 1045–1051 in proU sequence of the plasmid pHYD511 was disrupted (without any consequence to in vivo osmotic inducibility of the promoter) as follows: plasmid pHYD511 was linearised at the NdeI site by digestion with restriction enzyme NdeI, the ends were "blunted" using Klenow DNA polymerase and the four deoxynucleotide triphosphates, and the plasmid was recircularised with the aid of T4 DNA ligase and standard ligation-reaction conditions; the T4 DNA ligase was heat-inactivated and the DNA sample was ethanol-precipitated; this DNA sample was again digested with NdeI and the digestion mix was used to transform a preparation of DH5 competent cells to Amp<sup>r</sup>; DNA prepared from each of the ten individual transformants was then tested for the absence of NdeI site at proU 1045–1050 by restriction enzyme analysis, and one plasmid so identified, in which the NdeI site had been destroyed, was designated as pHYD512.

Figure 2:
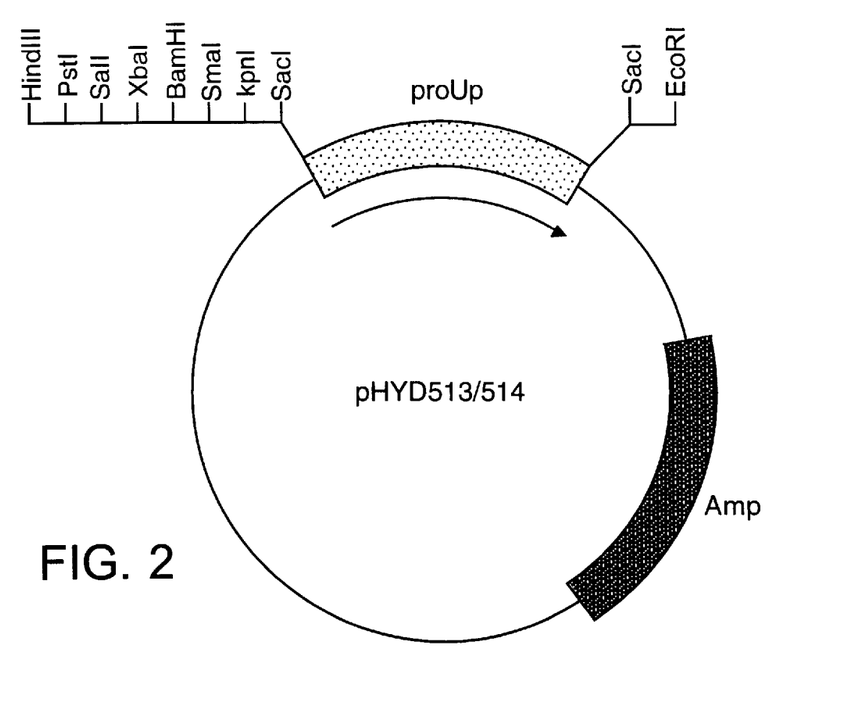
FIG. 2 depicts the physical map of pGEM3Z-derived plasmids pHYD513 and PHYD514.

The 1.25-kb proU sequence from pHYD512 was also subcloned on a SacI fragment into the SacI site of the vector pGEM-3Z and the resulting plasmid was designated as pHYD513. Thus the plasmids pHYD513 and pHYD514 harbour the cis regulatory region of proU (referred to in the other examples below as proUp) and unique restriction sites on either side of proUp as shown in FIG. 2 (which depicts the physical map of pGEM3Z-derived plasmids pHYD513 and pHYD514 showing the unique restriction sites available upstream and downstream of the proUp "cassette"; direction of transcription from proUp is marked by overhead arrow; both plasmids are identical except for the mutation of the NdeI site within proUp in pHYD513).

EXAMPLE 2

Construction of plasmid pHYD503 in which the proUp is linked to phage T7 RNA polymerase gene.

Figure 3:
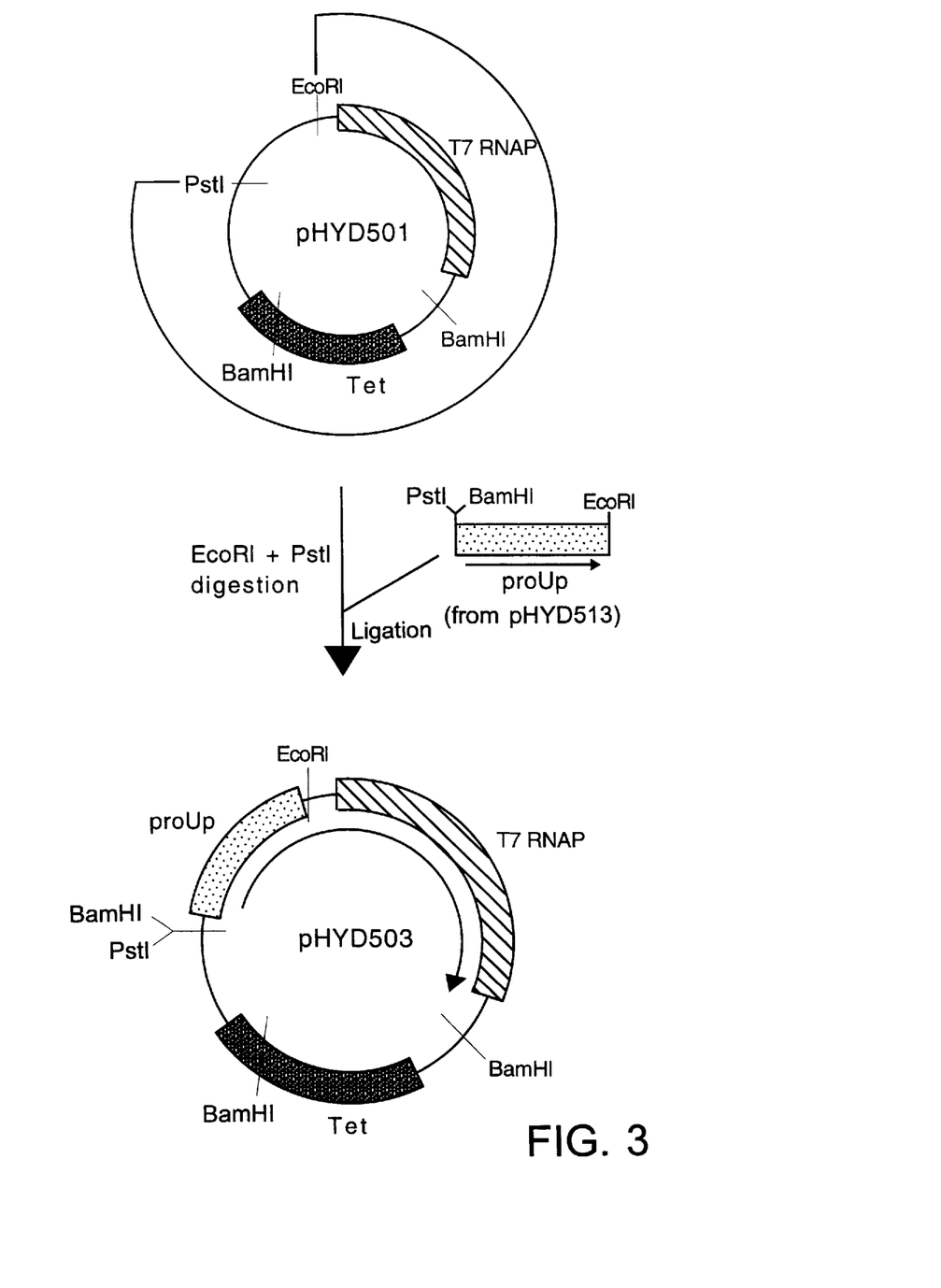
FIG. 3 depicts a schematic of the structure of plasmid pHYD501 and the steps in the construction of plasmid pHYD503 from plasmid pHYD501.

The plasmid pHYD501 is a P15A-replicon-based multi-copy plasmid encoding Tet<sup>r</sup> as the selective marker that carries the phage T7 RNA polymerase (T7 RNAP) gene without any upstream promoter (FIG. 3). To clone the proUp sequence upstream of the T7 RNAP gene in pHYD501, the plasmids pHYD501 and pHYD513 were each digested with EcoRI-PstI restriction enzymes. The enzymes were heat-inactivated and the two DNA samples were mixed, ethanol-precipitated, and ligation reactions were set up as per the standard protocol. The DH5-competent cells were transformed with the ligation mix. Tet<sup>r</sup> transformants were selected for, and these were screened for Amp<sup>s</sup> phenotype. Plasmid DNA was prepared from five Amp<sup>s</sup> Tet<sup>r</sup> transformants. Each of these DNA samples was digested with EcoRI-PstI restriction enzymes and analysed by agarose gel electrophoresis. All the samples showed two bands that were respectively 5.7 kb and 1.25 kb long, indicating that in every case the proU cis regulatory sequences had been cloned upstream of the T7 RNAP gene. One of these plasmid derivatives was designated as pHYD503 (see FIG. 3—containing a schematic depiction of structure of plasmid pHYD501 and of steps in construction of plasmid pHYD503 from pHYD501; not drawn to scale; arrows represent extent and direction of transcription from different promoters; transcription of the marker gene on the vector is not shown; positions of EcoRI, BamHI and PstI restriction sites in the various DNA molecules are marked; the arc depicts the fragments of pHYD501 used in the formation of pHYD503).

The plasmid pHYD503 was transformed into strain BL21 and Tetr transformants were selected on LBON-Tet plates. A single purified Tetr colony was then inoculated in 10 ml of LBON-Tet broth in a 100-ml Erlenmeyer flask and kept for overnight incubation at 37° C. in an environmental shaker. The next day, the culture was diluted 1:50 into 10 ml of fresh medium of the same composition and incubated as above. When the OD600 of the culture reached a value of around 0.8, the culture was divided equally into two 100-ml flasks, to one of which NaCl was added (from a 5 M stock in water) to a final concentration of 0.4 M to achieve osmotic induction whereas the other flask served as the uninduced control. Thereafter, the flasks were incubated at 37° C. in the environmental shaker for another 3 hours after which the cells in the cultures were harvested by centrifugation for 10 min at 4000 rpm in a bench-top centrifuge. The cell pellets were resuspended in 0.5 ml of hot (about 80° C.) sample buffer. The sample mix was boiled for 2 min, after which the samples were immediately transferred to ice and then stored at 20° C. The samples were then electrophoresed on a 6% sodium dodecyl sulphate-polyacrylamide gel and the gel was stained with Coomassie blue as per standard protocols. By this procedure, regulated overproduction of T7 RNA polymerase following NaCl addition to the BL21pHYD503 culture was clearly demonstrated, thereby substantiating the notion that proUp is useful in salt-inducible overproduction of heterologous proteins.

EXAMPLE 3
Integration of the novel proUp-T7 RNAP recombinant construct in a single copy into the chromosome of E.coli strain pop2249.

Figure 4:
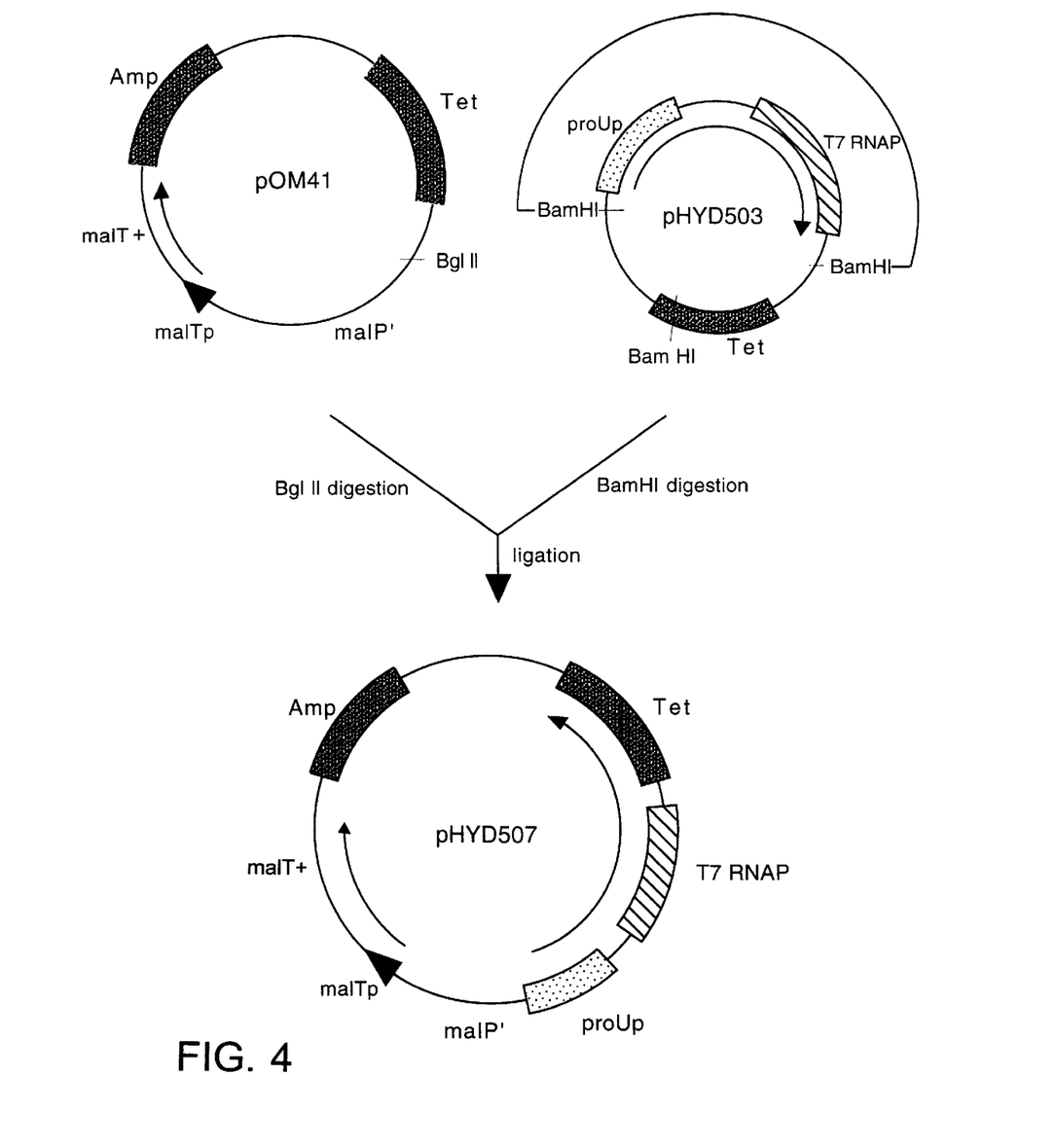
FIG. 4 depicts a schematic of the steps in the construction of plasmid pHYD507 from plasmid pHYD503.

For the insertion of the proUp-T7 RNAP fusion into the chromosome of E. coli, the integration technique as described by Raibaud et al. [Gene 29: 231–241 (1984)] was followed. In this system the insert to be integrated into the chromosome is cloned in the first step into the plasmid vector pOM41 such that the insert is flanked on the two sides by the sequences of the malP-malT locus. This Ampr plasmid vector also carries a transcriptional fusion between the promoterless malP gene and the gene encoding Tetr. Thus if any promoter-carrying insert is cloned in the right orientation into the vector, the resulting plasmid transformants are Tetr. For insertion of the proUp-T7 RNAP fragment into pOM41, the plasmid pHYD503 was digested with BamHI, and the 4.0-kb fragment bearing the proUp-T7 RNAP fusion was extracted by Geneclean after agarose gel electrophoresis. This fragment was then ligated with pOM41 DNA that had been linearised at the BglII site present in the malp gene (see FIG. 4—containing schematic depiction of steps in the construction of plasmid pHYD507 from plasmid pHYD503; symbols used being the same as those in FIG. 3). DH5 competent cells were transformed with the ligation mix and Ampr transformants were selected. These transformants were then screened for the phenotype of osmotically induced Tetr (expected from plasmids carrying the proUp-T7 RNAP insertion into pOM41 in the orientation depicted in FIG. 4), by streaking each in replicate on a pair of LBON-Tet plates one with and the other without 0.3 M NaCl. One plasmid, designated pHYD507, was saved in which the proUp-T7 RNAP fusion from pHYD503 had been inserted in the desired orientation into the BglII site of pOM41.

Figure 5:
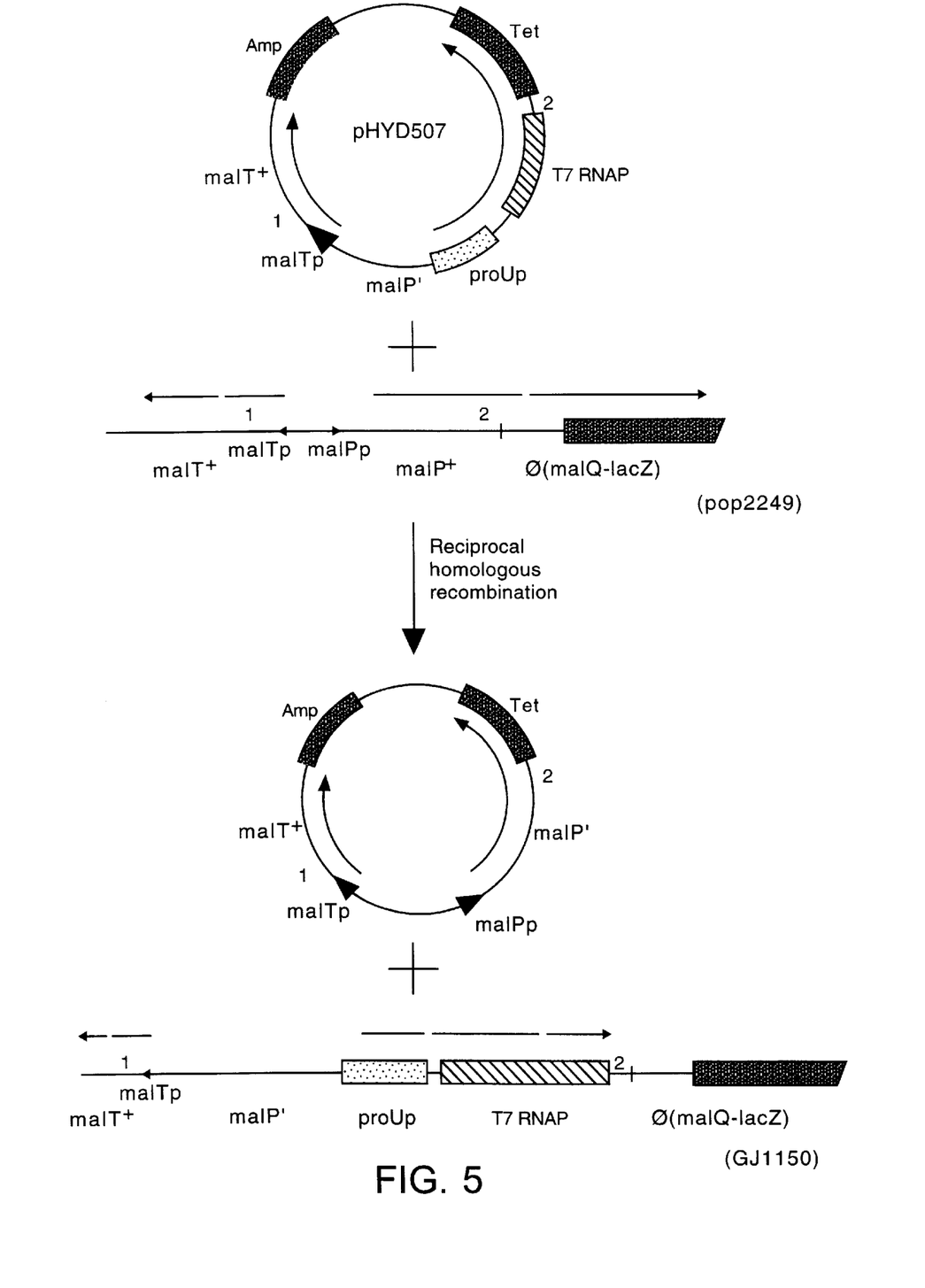
FIG. 5 depicts a schematic of the steps in the construction of strains GJI 150 by chromosomal integration of proUp-T7 RNAP fusion from plasmid pHYD507.

In the second step of this method (see FIG. 5—containing the schematic depiction of steps in construction of strains GJ1150 by chromosomal integration of proUp-T7 RNAP fusion from plasmid pHYD507; most symbols are explained in the legend to FIG. 3; the numerals 1 and 2 on the plasmid and chromosome identify homologous pairs of sites that serve as substrates for the postulated double cross-over reciprocal recombination event between the two replicons), the proUp-T7 RNAP fusion from the plasmid pHYD507 was transferred by homologous recombination into the malTPQ locus of the strain pop2249 (which strain also carries a malQ-lacZ gene fusion such that a hybrid protein with a-galactosidase activity is expressed following transcription from the promoter upstream of malp gene). For this purpose, the strain pop2249 was transformed with pHYD507, and Ampr transformants were selected on LBON-Amp plates. The transformants were then screened for Tet and Lac phenotype on LBON-based media. A majority of transformants were Lac+ and Tets under these conditions, but approximately 1–2%, in which presumably a reciprocal homologous recombination event had switched the proUp-T7 RNAP fusion from the plasmid into the chromosome and the malp promoter from the chromosome into the plasmid, had become Tetr and Lac-. The latter colonies (which were white and Tetr on the LBON medium supplemented with X-gal and tetracycline) were then subcultured twice on plates free of both the antibiotics, ampicillin and tetracycline, in order to obtain spontaneous plasmid-free segregants. The latter were identified on subsequent testing as Amps and Tets colonies. One representative strain was subsequently confirmed to carry the proUp-T7 RNAP fusion, as it was shown to be capable of overexpressing SSB protein upon osmotic induction of derivatives carrying the plasmid pGK2 (in which ssb gene is cloned downstream of the phage T7m10 promoter; see example 4). This strain was designated as GJ1150. Optionally, by methods (of transposon marker-tagging, gene transfer from GJ1150 and homologous recombination) already known in the art, ma1PQ-integrant derivatives of other strains such as BL21 or B834 can be constructed which carry the same proUp-T7 RNAP fusion that is present in the ma1PQ locus of GJ1150.

EXAMPLE 4
Overproduction of E. coli SSB protein in a derivative of GJ1150 by osmotic induction The strain GJ1150 was transformed with plasmid pGK2, which encodes Ampr as a selective marker and carries the E. coli ssb gene downstream of the phage T7 m10 promoter. Ampr transformants were selected on LBON-Amp broth in a 100-ml Erlenmeyer flask and kept for overnight incubation at 37° C. in an environmental shaker. The next day, the culture was diluted 1:50 into 10 ml of fresh LBON-Amp medium and incubated as above. When the OD600 of the culture reached a value of around 0.8 (corresponding to a cell density of approx. 5×108 cell/ml), the culture was divided equally into two 100-ml flasks, to one of which NaCl was added (from a 5M stock in water) to a final concentration of 0.3 M to achieve osmotic induction whereas the other flask served as the uninduced control. Thereafter, flasks were incubated at 37° C. in the environmental shaker for another 2 hours after which the cells in the cultures were harvested by centrifugation for 10 min at 4000 rpm in a bench-top centrifuge. The cells harvested from 2 ml of the culture were resuspended into 0.5 ml of hot (about 80° C.) sample buffer. The sample mix was boiled for 2 min, after which the samples were immediately transferred to ice and then stored at 20° C. To obtain the protein profile, the samples were electrophoresed on a 15% sodium dodecyl sulphate-polyacrylamide gel and stained with Coomassie blue as per standard protocols. By this procedure, regulated overproduction of *E. coli* SSB protein following NaCl addition to the GJ1150/pGK2 culture was clearly demonstrated.

By the same approach, and using appropriate plasmid-substitutes instead of pGK2, we have also successfully overproduced the Klenow fragment of *E. coli* DNA polymerase I, phage T7 DNA polymerase, the alpha-subunit of *E. coli* RNA polymerase, the yeast TATA-binding-protein, the rat lymphocyte protein tyrosine phosphatase PTP-S and a truncated version of a human potassium-channel protein. Furthermore, in light of the substantially homologous mechanisms that exist amongst various members of the family Enterobacteriaceae for gene expression, gene regulation (including proU osmotic regulation), and plasmid replication and maintenance, we expect that the strategy and the constructs described herein will confer salt-inducible overproduction of heterologous proteins in any bacterial strain within the family Enterobacteriaceae.

It may be noted that the examples given are merely illustrative of the uses, processes and products such as DNA sequences, vectors and strains claimed in this invention, and that the practice of the invention itself is not restricted to the examples described. We expect that additional configurations of the same invention could be achieved by one or more of the following modifications to the examples described above, using materials that are already known in the art or that are obtainable by methods known to the art:

(i) The cis regulatory elements of proU can be obtained from *E. coli* or *Salmonella typhimurium*, or from other species of the family Enterobacteriaceae with which the *E. coli* proU sequences share sufficient similarity to be identified either by DNA—DNA Southern blot hybridization or by polymerase chain reaction-amplification. Furthermore, mutant variations of these sequences or a different length of the native proU sequence, or a combination of both, that continue to exhibit substantial osmotic inducibility of transcription from the proU promoter(s) can also be used.

(ii) NaCl-inducible or osmotically-inducible promoters other than those for proU could be used. These promoters could be those of the other known NaCl-induced or osmotically induced genes listed in the section above on Prior art', or can be identified by methods known to the art that use reporter gene fusion-techniques or quantitative mRNA determinations under inducing and non-inducing growth conditions. Once such NaCl-inducible or osmotically-inducible genes have been identified, the promoters of the genes are obtainable by methods known in the art.

(iii) In the pursuit of the direct strategy indicated above, the operon fusion between an NaCl-inducible or osmotically-inducible promoter and a target gene can be cloned into other vectors including plasmids or phage for introduction into a suitable host bacterium.

(iv) In the pursuit of the indirect strategy indicated above, other transcription-activator genes and/or cognate activatable promoters that are known in the art can be used including genes for RNA polymerase and cognate promoters from any of the T7—related phages known to the art [Hausmann (1988) in The Bacteriophages (ed., R. Calendar), Plenum Press, New York, USA, pp. 259–289], with the said target gene then being fused to the cognate promoter activated by the particular transcription-activator protein. The said transcription-activator gene and its cognate activatable promoter are obtainable by the methods known in the art, and the said novel and the said second recombinant constructs can then also be made by methods known in the art.

(v) In the pursuit of the indirect strategy indicated above, the said novel recombinant construct can be cloned into other vectors including plasmids or phage for introduction into a suitable host bacterium. Likewise, the said novel recombinant construct can also be integrated into chromosomal locations other than ma1PQ in the strain, by any of a variety of methods known in the art [Gutterson and Koshland (1983) Proc. Natl. Acad. Sci USA 80: 4894–4898; Winans et al. (1985) J. Bacteriol. 161: 1219–1221; Parker and Marinus (1988) Gene 73: 531–535; Hamilton et al. (1989) J. Bacteriol. 171: 4617–4622; Deiderich et al. (1992) Plasmid 28: 14–24; Steed and Wanner (1993) J. Bacteriol. 175: 6797–6809].

(vi) In the pursuit of the direct strategy indicated above, any bacterium in which the said promoter exhibits NaCl-inducibility or osmotic-inducibility can be used as a suitable host strain.

(vii) In the pursuit of the indirect strategy indicated above, any bacterium in which the promoter of the said novel recombinant construct exhibits NaCl-inducibility or osmotic-inducibility and in which the said transcription-activator protein will activate transcription substantially only from the cognate promoter sequence introduced into it as part of the said second recombinant construct can be used as a suitable host strain.

(viii) In the pursuit of the indirect strategy indicated above, the said second recombinant construct can be cloned on any of a variety of vectors including plasmids or phage, or can even be integrated into the chromosome of the host strain by methods known in the art.

(ix) The target gene can encode any of a variety of heterologous gene products including proteins and polypeptides other than those listed in the examples, the said target gene being obtainable by methods known in the art. We have successfully used the processes described in this invention to overproduce, among others, the Klenow fragment of *E. coli* DNA polymerase I, phage T7 DNA polymerase, the alpha-subunit of *E. coli* RNA polymerase, the yeast TATA-binding-protein, the rat lymphocyte protein tyrosine phosphatase PTP-S and a truncated version of a human potassium-channel protein. We have also obtained evidence that some proteins which form intracellular inclusion bodies in *E. coli* upon overproduction by the use of prior-art methods, remain soluble upon overproduction by the NaCl-inducible processes described in this invention.

(x) Substances or a mixture that is comprised of substances (collectively referred to herein as "osmolytes") which are substantially impermeable to the plasma membrane of the host cell so as to be osmotically active on the said host cells, may be used instead of NaCl for induction of transcription from the said NaCl-inducible or osmotically-inducible promoter.

(xi) As variants of the two-tier regulatory cascade described in the pursuit of the indirect strategy indicated above, a multi-tier regulatory cascade can also be envisaged in which the said novel recombinant construct constitutes the first tier.

Furthermore, the practice of this invention includes, but is not restricted to, the processes of recombinant DNA manipulations and transformations; the composition of and volumes of low-osmolarity growth media; and the time of addition of, final concentration of, or duration of induction with NaCl or other osmolytes, that are described above.

a transcription activator protein-encoding DNA, the first promoter being positioned in the construct to direct expression of the transcription activator protein-encoding DNA, and the cis regulatory element being positioned in the construct for regulation of expression from the first promoter in said bacterium.

We claim:

1. A recombinant DNA construct comprising a plasmid or bacteriophage vector that can replicate in the bacterium, or can be integrated into the chromosome of the bacterium;
   a first bacterial promoter;
   a cis regulatory element that regulates transcription from the first promoter in the bacterium in response to NaCl concentration or other osmolyte concentration; and 2. A recombinant DNA construct according to claim 1 wherein the cis regulatory element is the *Escherichia coli* proU DNA sequence or a transcription regulating part thereof, or any DNA sequence that has the transcription-regulatory properties of the proU DNA sequence.

3. A recombinant DNA construct according to claim 1 wherein the transcription-activator protein is an enzymatically active RNA polymerase of bacteriophage T7.

4. A recombinant DNA construct of claim 3 comprising a BamHI-ended DNA fragment comprising
   (i) cis regulatory elements of *Escherichia coli* proU obtainable from plasmid pHYD513 on a PstI-EcoRI fragment, and
   (ii) a DNA segment encoding enzymatically active T7 RNA polymerase; wherein
      (a) said segment is linked in cis to said cis regulatory elements;
      (b) said segment is present on the larger of the two fragments obtainable from plasmid pHYD501 following PstI-EcoRI digestion; and
      (c) said BamHI-ended DNA fragment is obtainable from plasmid pHYD503.

5. A bacterial cell transformed with a first heterologous DNA element which is a recombinant DNA construct according to any one of claims 1–4.

6. A bacterial cell according to claim 5 further comprising a second heterologous DNA element which is part of, or separate from, the first DNA element, the second DNA element comprising DNA encoding a desired gene product positioned for expression under the control of a second promoter which is responsive to the transcription-activator protein expressed from the first DNA element.

7. The bacterial cell according to claim 6 in which the transcription-activator protein is an enzymatically active RNA polymerase of bacteriophage T7 and the second promoter is a bacteriophage T7 promoter.

8. A bacterial cell according to claim 7 in which the second promoter is the m10 bacteriophage T7 promoter.

9. A bacterial cell according to claim 5, in which the recombinant DNA construct is either (i) integrated into the bacterial chromosome or (ii) present on a recombinant plasmid or phage vector that is capable of autonomous replication within the said bacterium.

10. A bacterial cell according to claim 5 wherein the bacterium is a member of the family Enterobacteriaceae.

11. A bacterial cell according to claim 10 wherein the bacterium is a member of the species *Escherichia coli*.

12. A method for expressing a heterologous gene encoding a desired gene product, the gene product being an RNA or polypeptide, said method comprising the steps of:
   (a) providing the bacterial cell of claim 6;
   (b) growing a culture of the bacterial cell in a low-osmolarity medium;
   (c) adding to the culture NaCl or other osmolyte to induce the expression of the transcription-activator protein, which then causes expression of the desired gene product from the second DNA element; and
   (d) isolating the desired gene product.

13. A method as claimed in claim 12 wherein the first heterologous DNA element comprises a BamHI-ended DNA fragment obtainable from plasmid pHYD503, which fragment comprises
   (i) the cis regulatory elements of *Escherichia coli* proU obtainable from plasmid pHYD513 on a PstI-EcoRI fragment, and
   (ii) a DNA segment that carries the sequence encoding enzymatically active T7 RNA polymerase and is present on the larger of the two fragments obtainable from plasmid pHYD501 following PstI-EcoRI digestion, said DNA segment being linked in cis to said cis regulatory elements.

14. A method as claimed in claim 12 wherein the cell belongs to a bacterial species of the family Enterobacteriaceae.

15. A method as claimed in claim 14 wherein the cell belongs to the species *Escherichia coli*.

16. A method according to claim 13 in which the bacterial cell belongs to the species *Escherichia coli*, and the BamHI-ended DNA fragment is integrated into the ma1PQ locus on the chromosome.

17. A method according to claim 16 in which the bacterial cell is *E. coli* strain GJ1150.

18. *Escherichia coli* strain GJ1150, in which the BamHI-ended DNA fragment according to claim 4 is integrated into the ma1PQ locus of the chromosome.

19. A method for obtaining a transformed bacterium harboring recombinant DNA for expressing a heterologous gene by induction, comprising the steps of:
   (a) providing the recombinant DNA construct of any one of claims 1–4;
   (b) transforming the recombinant DNA construct into a host bacterium in which the construct can be maintained;
   (c) identifying clones carrying the correct recombinant DNA construct; and
   (d) obtaining a transformed bacterium in which the recombinant DNA construct is either (i) integrated into the bacterial chromosome or (ii) present on a recombinant plasmid or phage vector that is capable of autonomous replication within said host bacterium.

20. A method as claimed in claim 19 wherein the cis regulatory element is the *Escherichia coli* proU DNA sequence or a transcription regulating part thereof, or any DNA sequence that has the transcription-regulatory properties of the proU DNA sequence.

21. A method as claimed in claim 19 wherein the transcription-activator protein is an enzymatically active RNA polymerase of bacteriophage T7.

22. A method for obtaining a transformed bacterium harboring recombinant DNA for expressing a heterologous gene by induction, comprising the steps of:
   preparing the recombinant DNA construct of any one of claims 1–4 by
   (a) obtaining and cloning a first DNA segment that carries the sequence encoding a promoter or promoters along with cis regulatory elements that permit NaCl-inducible or osmotically inducible initiation of transcription from said promoter or promoters in a suitable host bacterium;
   (b) linking said first DNA segment with a second DNA segment that carries a sequence encoding a transcription-activator protein such that synthesis of said protein, in derivatives of said host bacterium carrying said recombinant DNA construct, is exclusively or nearly exclusively dependent on transcription initiated from said promoter or promoters; and also such that said recombinant DNA construct is covalently contiguous with the DNA sequence of a vector such as plasmid or phage;
   (c) transforming the ligation mixture into a suitable strain in which said vector can replicate autonomously and be maintained; and
   (d) identifying clones carrying the correct recombinant construct; and
   obtaining a transformed derivative bacterium in which said recombinant DNA construct is either (i) integrated into the bacterial chromosome or (ii) present on a recombinant plasmid or phage vector that is capable of autonomous replication within said host bacterium.

23. A method as claimed in claim 22 wherein:
(a) the recombinant DNA construct is comprised of an *Escherichia coli* proU-T7 RNA polymerase fusion;
(b) the bacterium is *Escherichia coli*; and
(c) the first DNA segment carries the *Escherichia coli*-derived proU cis regulatory elements and is obtainable from plasmid pHYD513 or pHYD514 by PstI-EcoRI digestion; the second DNA segment carries a sequence encoding an enzymatically active T7 RNA polymerase and is present on plasmid pHYD501; the recombinant DNA construct is generated by ligating the PstI-EcoRI-ended first DNA segment with the larger of the two fragments generated following PstI-EcoRI digestion of plasmid pHYD501; and plasmids carrying the said recombinant DNA construct, such as pHYD503, are identified following transformation of a suitable strain with the ligation mixture and selection for tetracycline-resistance.

24. A method for obtaining integration of the recombinant DNA construct of claim 4 into the malPQ locus of the chromosome of an *Escherichia coli* bacterium, said method comprising the steps of:

(a) ligating the BamHI-ended DNA fragment carrying the proU-T7 RNA polymerase fusion and obtainable from plasmid pHYD503, with BglII-digested pOM41 DNA;
(b) identifying a recombinant plasmid, such as pHYD507, in which the proU promoter on the insert is transcribed in the same direction as the promoterless tet gene in pOM41;
(c) transforming said recombinant plasmid into strain pop2249 and identifying derivatives that are tetracycline-resistant, ampicillin-resistant and Lac- at low osmolarity, in which the proU-T7 RNA polymerase fusion construct has been transferred by reciprocal homologous recombination into the malPQ locus; and
(d) subsequently identifying integrant colonies, such as GJ1150, in which the ampicillin-resistance and tetracycline-resistance markers have been lost following spontaneous loss of the pOM41-derived plasmid replicon.

25. The method of claim 24 further comprising transferring, by gene transfer and homologous recombination, the malPQ locus carrying the integrated proU-T7 RNA polymerase fusion construct from these integrant strains into other strains of *Escherichia coli*.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
      ( A ) LENGTH: 1260 base pairs
      ( B ) TYPE: nucleic acid
      ( C ) STRANDEDNESS: single
      ( D ) TOPOLOGY: linear    ( i i ) MOLECULE TYPE: cDNA    ( x i ) SEQUENCE DESCRIPTION: SEQ ID NO:1:

```
GAGCTCGAAT  TAATTCCCGC  CAAATAGCTT  TTTATCACGC  AAATAATTTG  TGGTGATCTA    60
CACTGATACT  CTGTTGCATT  ATTCGCCTGA  AACCACAATA  TTCAGGCGTT  TTTTCGCTAT   120
CTTTGACAAA  AAATATCAAC  TTTCTCGATT  TGCTCTCAGC  CCTTATATCA  CGGGAAATTC   180
CGGCGATTTG  CTCGCATCAA  TATTCATGCC  ACATTTGCCA  TCAGGGGTTG  CCTCAGATTC   240
TCAGTATGTT  AGGGTAGAAA  AAAGTGACTA  TTTCCATTGG  GTAATATATC  GACATAGACA   300
AATAAAGGAA  TCTTTCTATT  GCATGGCAAT  TAAATTAGAA  ATTAAAAATC  TTTATAAAAT   360
ATTTGGCGAG  CATCCACAGC  GAGCGTTCAA  ATATATCGAA  CAAGGACTTT  CAAAAGAACA   420
AATTCTGGAA  AAAACTGGGC  TATCGCTTGG  CGTAAAAGAC  GCCAGTCTGG  CCATTGAAGA   480
AGGCGAGATA  TTTGTCATCA  TGGGATTATC  CGGCTCGGGT  AAATCCACAA  TGGTACGCCT   540
TCTCAATCGC  CTGATTGAAC  CCACCCGCGG  GCAAGTGCTG  ATTGATGGTG  TGGATATTGC   600
CAAAATATCC  GACGCCGAAC  TCCGTGAGGT  GCGCAGAAAA  AAGATTGCGA  TGGTCTTCCA   660
GTCCTTTGCC  TTAATGCCGC  ATATGACCGT  GCTGGACAAT  ACTGCGTTCG  GTATGGAATT   720
GGCCGGAATT  AATGCCGAAG  AACGCCGGGA  AAAAGCCCTT  GATGCACTGC  GTCAGGTCGG   780
GCTGGAAAAT  TATGCCCACA  GCTACCCGGA  TGAACTCTCT  GGCGGGATGC  GTCAACGTGT   840
GGGATTAGCC  CGCGCGTTAG  CGATTAATCC  GGATATATTA  TTAATGGACG  AAGCCTTCTC   900
GGCGCTCGAT  CCATTAATTC  GCACCGAGAT  GCAGGATGAG  CTGGTAAAAT  TACAGGCGAA   960
ACATCAGCGC  ACCATTGTCT  TTATTTCCCA  CGATCTTGAT  GAAGCCATGC  GTATTGGCGA  1020
CCGAATTGCC  ATTATGCAAA  ATGGTGAAGT  GGTACAGGTC  GGCACACCGG  ATGAAATTCT  1080
CAATAATCCG  GCGAATGATT  ATGTCCGTAC  CTTCTTCCGT  GGCGTTGATA  TTAGTCAGGT  1140
ATTCAGTGCG  AAAGATATTG  CCCGCCGGAC  TTAATTCGTA  AAACCCCTGG  CTTCGGCCCA  1200
CGTTCGGCAC  TGAAATTATT  GCAGGATGAA  GATCGCGAAT  ATGGCTACGT  TATCGAGCTC  1260
```